(12) United States Patent
Neumann

(10) Patent No.: US 11,942,207 B2
(45) Date of Patent: Mar. 26, 2024

(54) ARTIFICIAL INTELLIGENCE METHODS AND SYSTEMS FOR GENERATING ZOOLOGICAL INSTRUCTION SETS FROM BIOLOGICAL EXTRACTIONS

(71) Applicant: KPN Innovations, LLC, Lakewood, CO (US)

(72) Inventor: Kenneth Neumann, Lakewood, CO (US)

(73) Assignee: KPN Innovations, LLC, Lakewood, CO (US)

( * ) Notice: Subject to any disclaimer, the term of this patent is extended or adjusted under 35 U.S.C. 154(b) by 596 days.

(21) Appl. No.: 16/825,248

(22) Filed: Mar. 20, 2020

(65) Prior Publication Data
US 2021/0295951 A1  Sep. 23, 2021

(51) Int. Cl.
*G16H 20/60*  (2018.01)
*B01D 11/02*  (2006.01)
(Continued)

(52) U.S. Cl.
CPC ............ *G16H 20/60* (2018.01); *G06F 18/24* (2023.01); *G06N 20/00* (2019.01); *G06V 10/764* (2022.01);
(Continued)

(58) Field of Classification Search
CPC ........ G06N 20/00; G06N 20/10; G06N 7/005; G06V 10/764; G06V 10/762;
(Continued)

(56) References Cited

U.S. PATENT DOCUMENTS 6,493,641 B1  12/2002  Singh et al.
7,873,482 B2  1/2011  Stefanon et al.
(Continued)

FOREIGN PATENT DOCUMENTS

CN      106407711       2/2017
WO    WO-2009105061 A1 *  8/2009   ............ C12M 41/46
(Continued)

OTHER PUBLICATIONS

Jennifer Wrye "Nutritionism and the Making of Modern Pet Food", Carleton University, Ottawa, Ontario, 2012. (Year: 2012).*
(Continued)

*Primary Examiner* — Pan G Choy
(74) *Attorney, Agent, or Firm* — Caldwell Intellectual Property Law

(57) ABSTRACT

An artificial intelligence system for generating zoological instruction sets from biological extractions. The system includes a computing device, configured to retrieve a biological extraction pertaining to an animal. The computing device is further configured to generate a zoological classifier wherein the zoological classifier utilizes a biological extraction as an input and outputs a zoological profile. The computing device is further configured to receive a zoological input from a remote device, wherein the zoological input identifies a zoological habit. The computing device is further configured to select a zoological machine-learning model utilizing a zoological input, wherein the zoological machine-learning model utilizes a zoological profile as an input and outputs a zoological instruction set. The computing device is further configured to calculate a zoological instruction set utilizing a zoological machine-learning model.

16 Claims, 5 Drawing Sheets

(51) Int. Cl.
  *G06F 18/24* (2023.01)
  *G06N 20/00* (2019.01)
  *G06V 10/764* (2022.01)
  *G06V 10/774* (2022.01)
  *G06V 20/69* (2022.01)
  *G16B 40/00* (2019.01)

(52) U.S. Cl.
  CPC .......... *G06V 10/774* (2022.01); *G06V 20/698* (2022.01); *G16B 40/00* (2019.02); *B01D 11/0207* (2013.01)

(58) Field of Classification Search
  CPC .... G06V 10/774; G06V 20/698; G16H 50/20; G16H 50/70; G16H 10/60; G16H 20/60; Y02A 90/10; B01D 11/0207; G06K 9/6215; G06K 9/6218; G06K 9/623; G06K 9/6267; G06K 9/6278; G16B 40/00
  See application file for complete search history.

(56) References Cited

U.S. PATENT DOCUMENTS

| | | | |
|---|---|---|---|
| 9,420,809 B2 | 8/2016 | Donavon et al. | |
| 10,115,110 B2 | 10/2018 | Gibbs | |
| 10,354,342 B2 | 7/2019 | Kuper et al. | |
| 2005/0051109 A1* | 3/2005 | Fantin | A01K 11/004 119/721 |
| 2006/0045909 A1* | 3/2006 | Friesen | G16B 20/40 435/6.12 |
| 2009/0299821 A1 | 12/2009 | Willcocks et al. | |
| 2012/0004854 A1* | 1/2012 | Fernandez | G16B 20/20 436/64 |
| 2014/0141134 A1 | 5/2014 | Johnson et al. | |
| 2015/0072048 A1 | 3/2015 | Potthoff et al. | |
| 2015/0159215 A1 | 6/2015 | Takimoto | |
| 2015/0242566 A1 | 8/2015 | Samer | |
| 2018/0065248 A1* | 3/2018 | Barral | G06N 20/00 |
| 2018/0068083 A1* | 3/2018 | Cohen | G16B 50/30 |

FOREIGN PATENT DOCUMENTS

| | | | |
|---|---|---|---|
| WO | WO-2018109725 A1 * | 6/2018 | .......... A01K 29/005 |
| WO | WO-2019002881 A1 * | 1/2019 | ............ A01K 61/10 |
| WO | WO2019143714 | 7/2019 | |

OTHER PUBLICATIONS

Vandersommers "The National Zoological Park and the Transformation of Humanism in Nineteenth-Century America", The Ohio State University. ProQuest Dissertations Publishing, 2014. 27725707. (Year: 2014).*

Vandersommers "The National Zoological Park and the Transformation of Humanism in Nineteenth-Century America", The Ohio State University. ProQuest Dissertations Publishing, 2014. (Year: 2014).* https://www.cambridge.org/core/services/aop-cambridge-core/content/view/4E12C582355F2F317D56FE60BB189C0D/S1751731118002288a.pdf/review_precision_nutrition_of_ruminants_approaches_challenges_and_potential_gains.

* cited by examiner

ARTIFICIAL INTELLIGENCE METHODS AND SYSTEMS FOR GENERATING ZOOLOGICAL INSTRUCTION SETS FROM BIOLOGICAL EXTRACTIONS

FIELD OF THE INVENTION

The present invention generally relates to the field of artificial intelligence. In particular, the present invention is directed to artificial intelligence methods and systems for generating zoological instruction sets from biological extractions.

BACKGROUND

Informed decisions regarding health and longevity of animals can be challenging. Frequently, animals are fed at erratic schedules, and may not receive optimized nutrition and supplementation. There remains to be seen, a way to create customized instruction sets for animals, based on an animal's biological extraction.

SUMMARY OF THE DISCLOSURE

In an aspect, an artificial intelligence system for generating zoological instruction sets from biological extractions, the system comprising a computing device, the computing device designed and configured to retrieve, a biological extraction pertaining to an animal. The computing device is further configured to generate a zoological classifier wherein the zoological classifier utilizes the biological extraction as an input and outputs a zoological profile. The computing device is further configured to receive a zoological input from a remote device wherein the zoological input identifies a zoological habit. The computing device is further configured to select a zoological machine-learning model utilizing the zoological input wherein the zoological machine-learning model utilizes the zoological profile as an input and outputs a zoological instruction set. The computing device is further configured to calculate a zoological instruction set utilizing the zoological machine-learning model.

In an aspect, an artificial intelligence method of generating zoological instruction sets from biological extractions, the method comprising retrieving, by a computing device, a biological extraction pertaining to an animal. The method further comprises generating, by the computing device, a zoological classifier wherein the zoological classifier utilizes the biological extraction as an input and outputs a zoological profile. The method further comprises receiving by the computing device, a zoological input from a remote device wherein the zoological input identifies a zoological habit. The method further comprises selecting by the computing device, a zoological machine-learning model utilizing the zoological input wherein the zoological machine-learning model utilizes the zoological profile as an input and outputs a zoological instruction set. The method further comprises calculating by the computing device, a zoological instruction set utilizing the zoological machine-learning model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to artificial intelligence systems and methods for generating zoological instruction sets from biological extractions. In an embodiment, a computing device retrieves a biological extraction pertaining to an animal. A computing device generates a zoological classifier, wherein the zoological classifier utilizes a biological extraction as an input and outputs a zoological profile. The computing device receives a zoological input, identifying a zoological habit. For example, a zoological input may identify any nutritional habits of an animal, such as how many times each day the animal consumes meals. A zoological input may also identify any supplement habits of an animal, such as what types of supplements an animal may consume. A computing device selects a zoological machine-learning model, and calculates a zoological instruction set utilizing the selected zoological machine-learning model.

Figure 1:
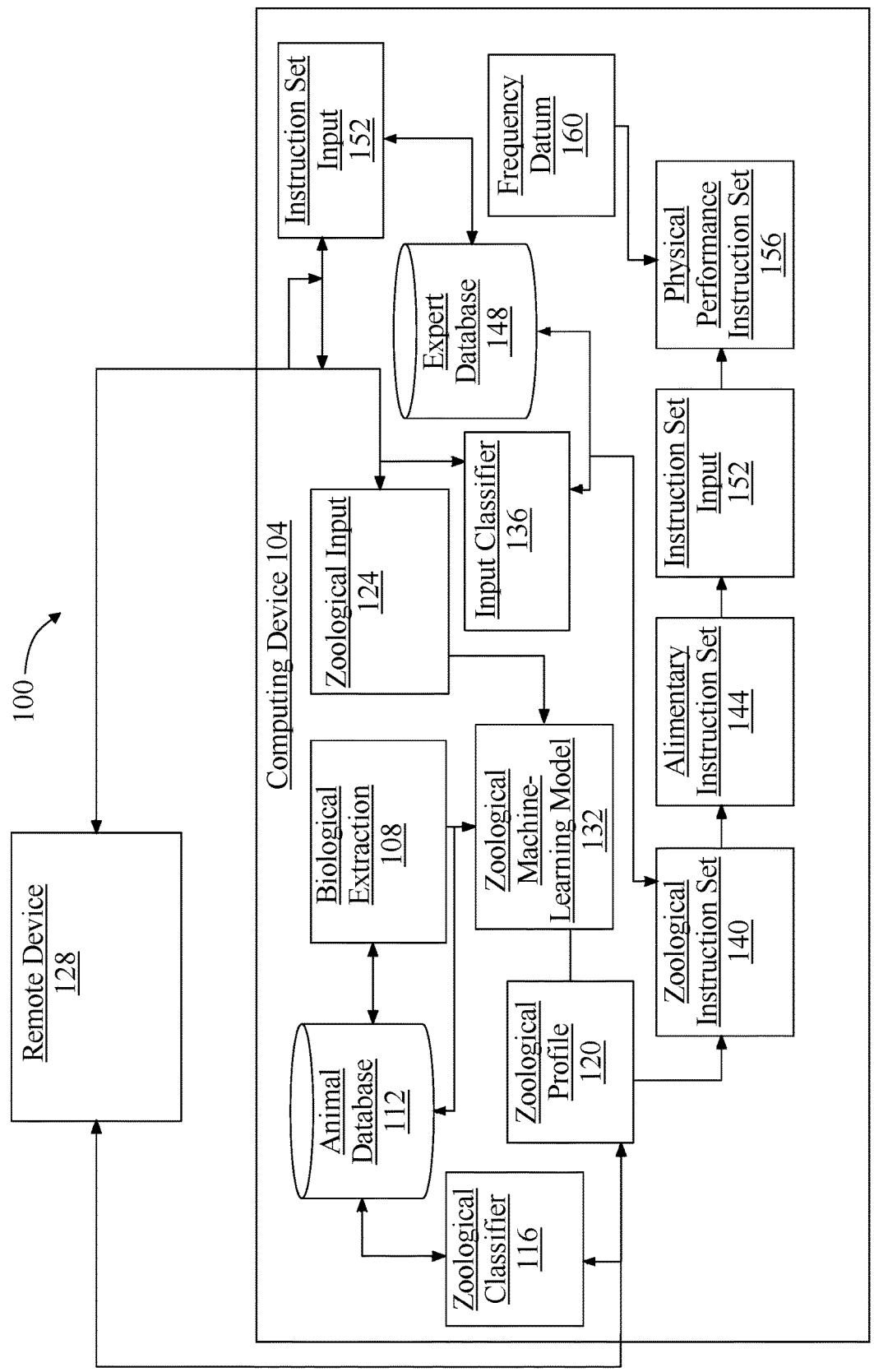
FIG. 1 is a block diagram illustrating an exemplary embodiment of an artificial intelligence system for generating zoological instruction sets from biological extractions.

Referring now to FIG. 1, an exemplary embodiment of an artificial intelligence system 100 for generating zoological instruction set 140 from biological extraction 108 is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker, in an embodiment, this may enable scalability of system 100 and/or computing device 104.

Continuing to refer to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to retrieve a biological extraction 108 pertaining to an animal. A "biological extraction" as used in this disclosure is an element of data including at least an element of physiological data of an organism. As used in this disclosure, "physiological data" is any data indicative of an animal's physiological state; physiological state data may be evaluated with regard to one or more measures of health of an animal's body, one or more systems within an animal's body such as a circulatory system, a digestive system, a nervous system, or the like, one or more organs within an animal's body, and/or any other subdivision of an animal's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in an animal's blood and/or in a blood sample, hemoglobin levels, hematocrit representing a percentage of blood in an animal and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, animal tests, animal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from animal interactions with animals, documents, and/or computing devices 104; for instance, animal patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module as described in this disclosure. As a non-limiting example, biological extraction 108 may include a psychological profile; the psychological profile may be obtained utilizing a questionnaire performed by the animal.

Still referring to FIG. 1, physiological state data may include genomic data, including deoxyribonucleic acid (DNA) samples and/or sequences, such as without limitation DNA sequences or other genetic sequences contained in one or more chromosomes in animal cells. Genomic data may include, without limitation, ribonucleic acid (RNA) samples and/or sequences, such as samples and/or sequences of messenger RNA (mRNA) or the like taken from animal cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of an animal, which as used herein includes any data describing any microorganism and/or combination of microorganisms living on or within an animal, including without limitation biomarkers, genomic data, proteomic data, and/or any other metabolic or biochemical data useful for analysis of the effect of such microorganisms on other physiological state data of an animal, as described in further detail below.

With continuing reference to FIG. 1, physiological state data may include one or more animal-entered descriptions of an animal's physiological state. One or more animal-entered descriptions may include, without limitation, animal descriptions of symptoms, which may include without limitation current or past physical, psychological, perceptual, and/or neurological symptoms, animal descriptions of current or past physical, emotional, and/or psychological problems and/or concerns, animal descriptions of past or current treatments, including therapies, nutritional regimens, exercise regimens, pharmaceuticals or the like, or any other animal-entered data that an animal may provide to a medical professional when seeking treatment and/or evaluation, and/or in response to medical intake papers, questionnaires, questions from medical professionals, or the like. Physiological state data may include any physiological state data, as described above, describing any multicellular organism living in or on an animal including any parasitic and/or symbiotic organisms living in or on the animals; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by an animal in a form or similar graphical animal interface object; one or more entries may include, without limitation, animal responses to questions on a psychological, behavioral, animality, or cognitive test. For instance, at least a server may present to animal a set of assessment questions designed or intended to evaluate a current state of mind of the animal, a current psychological state of the animal, an animality trait of the animal, or the like; at least a server may provide animal-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, an animality test scoring such as a Myers-Briggs test protocol, or other assessments that may occur to animals skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, animality, or other assessments. Third-party device may include a device operated by an informed advisor. An informed advisor may include any medical professional who may assist and/or participate in the medical treatment of an animal. An informed advisor may include a veterinarian, medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Animals skilled in the art, upon reviewing the entirety of this disclosure, will be aware of various additional examples of at least a physiological sample consistent with this disclosure.

With continued reference to FIG. 1, physiological data may include one or more animal body measurements. A "animal body measurement" as used in this disclosure, includes a measurable indicator of the severity, absence, and/or presence of a disease state. A "disease state" as used in this disclosure, includes any harmful deviation from the normal structural and/or function state of an animal. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, animal body measurements may be related to particular dimensions of the animal body. A "dimension of the animal body" as used in this disclosure, includes one or more functional body systems that are impaired by disease in an animal body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the animal body may include but are not limited to epigenetics, gut-wall, microbiome, nutrients, genetics, and/or metabolism.

With continued reference to FIG. 1, epigenetic, as used herein, includes any animal body measurements describing changes to a genome that do not involve corresponding changes in nucleotide sequence. Epigenetic body measurement may include data describing any heritable phenotypic. Phenotype, as used herein, include any observable trait of an animal including morphology, physical form, and structure. Phenotype may include an animal's biochemical and physiological properties, behavior, and products of behavior. Behavioral phenotypes may include cognitive, animality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when an animal is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile, cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of animal tissues and biofluids. For example, animal tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a animal being without causing harm or disease. Microbiome may include organisms that are not harmful but rather harm the animal when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as *Methanobrevibacter* smithies' and Methanosphaera stadtmanae. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's *muciniphila, Anaerotruncus colihominis*, bacteriology, *Bacteroides* vulgates', *Bacteroides-Prevotella, Barnesiella* species, *Bifidobacterium* longarm, *Bifidobacterium* species, *Butyrivbrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, Firmicutes to Bacteroidetes ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living an animal's gut including bacteria, viruses, archaea, yeast, fungi, parasites, and bacteriophages. Microbiome body measurement may include DNA and RNA sequences from live microorganisms that may impact an animal's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease-causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of an animal's body. This may include for example, lactose intolerance breath tests, methane-based breath tests, hydrogen-based breath tests, fructose-based breath tests, *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the animal body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify an animal's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within an animal's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vasodilation and vasoconstriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fullness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify an animal's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze an animal's resting metabolic rate or number of calories that an animal's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Animals skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from an animal body of an animal. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with an animal body of an animal such as a microchip embedded in an animal's skin, a sensor in contact with an animal's skin, a sensor located on an animal's tooth, and the like. Physiological data may be obtained from a physically extracted sample. A physical sample may include a signal from a sensor configured to detect physiological data of an animal and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MM) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100. Animal data may include a profile, such as a psychological profile, generated using previous item selections by the animal; profile may include, without limitation, a set of actions and/or navigational actions performed as described in further detail below, which may be combined with biological extraction 108 data and/or other animal data for processes such as classification to animal sets as described in further detail below.

Still referring to FIG. 1, retrieval of biological extraction 108 may include, without limitation, reception of biological extraction 108 from another computing device 104 such as a device operated by a medical and/or diagnostic professional and/or entity, an animal client device, and/or any device suitable for use as a third-party device as described in further detail below. Biological extraction 108 may be received via a questionnaire posted and/or displayed on a third-party device as described below, inputs to which may be processed as described in further detail below. Alternatively or additionally, biological extraction 108 may be stored in and/or retrieved from an animal database 112. Animal database 112 may include any data structure for ordered storage and retrieval of data, which may be implemented as a hardware or software module. An animal database 112 may be implemented, without limitation, as a relational database, a key-value retrieval datastore such as a NOSQL database, or any other format or structure for use as a datastore that an animal skilled in the art would recognize as suitable upon review of the entirety of this disclosure. An animal database 112 may include a plurality of data entries and/or records corresponding to one or more biological extraction 108 as described above. Data entries in an animal database 112 may be flagged with or linked to one or more additional elements of information, which may be reflected in data entry cells and/or in linked tables such as tables related by one or more indices in a relational database. Animals skilled in the art, upon reviewing the entirety of this disclosure, will be aware of various ways in which data entries in an animal database 112 may reflect categories, cohorts, and/or populations of data consistently with this disclosure. Animal database 112 may be located in memory of computing device 104 and/or on another device in and/or in communication with system 100.

With continued reference to FIG. 1, and as noted above, retrieval of biological extraction 108 may be performed multiple sequential and/or concurrent times, and any process using biological extraction 108 as described below may be performed multiple sequential and/or concurrent times; likewise, biological extract may include multiple elements of physiological data, which may be used in combination for any determination and/or other processes as described below.

With continued reference to FIG. 1, an "animal," as used in this disclosure, includes any domestic or tamed animal kept for companionship, pleasure, and/or consumption by human beings. An animal may include a pet kept in one's house or one one's property. For instance and without limitation, an animal may include a rabbit, a cat, a dog, a ferret, a fish, a sugar glider, a bird, a turtle, a guinea pig, a hamster, a hedgehog, a goat, a horse, a gerbil, a chinchilla, a mouse, a rat, a reptile, a llama, a sheep, a tortoise, a common iguana, a lizard, a bearded dragon, cattle, a parrot, an amphibian, a rodent, a gecko, a puppy, a mammal, saltwater fish, a snake, and the like. An animal may include any animal commonly eaten by human beings, including any domesticated meat and/or fish animals that may include a bovine, a camel, a dog, a goat, a deer, a cat, a donkey, a horse, a rabbit, a kangaroo, a sheep, a guinea pig, a pig, a frog, a chicken, a duck, a goose, a turkey, a quail, a pigeon, an ostrich, an emu, a fish, a lobster, a shrimp, an oyster, a mussel, an alligator, a crocodile, a turtle, and the like.

With continued reference to FIG. 1, computing device 104 is configured to generate a zoological classifier. A "classifier," as used in this disclosure, is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. Zoological classifier 116, utilizes a biological extraction 108 as an input and outputs a zoological profile 120. Computing device 104 may generate zoological classifier 116 using a classification algorithm, defined as a process whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, "training data," as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, computing device 104 may be configured to generate zoological classifier 116 using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(AB)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate zoological classifier 116 using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting example, K-nearest neighbors algorithm may be configured to classify an input vector containing a biological extraction 108 to an output vector containing a zoological profile 120.

With continued reference to FIG. 1, a "zoological profile," as used in this disclosure, is data describing one or more animal characteristics and/or traits, including without limitation characteristics and/or traits attributed to an animal's biological extraction 108. An animal characteristic and/or trait may identify one or more attributes that can be expected of a given animal. An animal characteristic may be identified utilizing an animal's biological extraction 108 and a first classification algorithm. An animal characteristic may identify a metabolic characteristic such as how many calories a day an animal needs to sustain life. An animal characteristic may identify an activity characteristic, which may identify how active an animal should be on any given day. An animal characteristic may identify one or more nutrients that an animal may not absorb well and may need to supplement with. An animal characteristic may identify one or more foods that may not be tolerated by an animal. For instance and without limitation, an animal's biological extraction 108 may show the animal has reduced gastric acid production and as such, a classification algorithm may classify the animal to a zoological profile 120 that identifies an animal characteristic that reflects that the animal should not consume foods heavily digested in the presence of gastric acid, including meat, oils, and calcium rich foods such as milk and cheese.

With continued reference to FIG. 1, computing device 104 is configured to receive a zoological input 124 from a remote device 128. A "zoological input," as used in this disclosure, is data describing any zoological habit, where a "zoological habit" is any habit performed by an animal and/or a third-party who may provide care to an animal. A zoological input 124 may be generated by a third-party, which may include any human being that may care for an animal. A habit may include any feeding habits, any exercise habits, any wellness habits, any supplement habits, any medication habits, any alternative health habits and the like. A habit may identify a nourishment element, where a nourishment element may identify any habit relating to food and nutrition of an animal. For instance and without limitation, a nourishment element may identify if an owner cooks food from scratch for an animal, if an owner buys commercial animal food, how often an owner feeds an animal, what types of foods an animal enjoys eating, what types of foods an animal dislikes, any particular dietary requests of an animal, and the like. One or more zoological input 124 may be stored within animal database 112. For instance and without limitation, a zoological input 124 may describe an animal that is fed food cooked from scratch by an owner. In yet another non-limiting example, a zoological input 124 may describe an animal that is fed commercial food three times each day. A habit may identify a supplementation element, where a supplementation element may identify any habit relating to supplements. Supplements may include products consumed by an animal that contain a dietary ingredient. Dietary ingredients may include any vitamin, mineral, nutrient, homeopathic, amino acid, herb, botanical, nutraceutical, enzyme, health food, medical food, and the like. Supplements may contain dietary ingredients sourced from food, synthesized in a laboratory, and/or sourced in combination. For instance and without limitation, a supplement may include oregano oil administered as a natural anti-microbial administered to a flock of chickens to prevent the transmission of disease. In yet another non-limiting example, a supplement may include a glucosamine supplement given to an aging dog, to relieve arthritic joint pain. A supplementation element may identify one or more supplements administered to an animal. For example, a supplementation element may identify a chewable iron tablet given to an anemic cat. A supplementation element may identify a dose indicating a particular strength of supplement given, a frequency, a quantity, directions for use and the like. A zoological input 124 may include one or more additional habits for a particular animal, that may indicate any other area of an animal's lifestyle. For example, a zoological input 124 may indicate a fitness level of an animal, such as a dog that may be very active or a cat that stays indoors and doesn't move much throughout the day.

With continued reference to FIG. 1, a zoological input 124 may be received from a remote device 128, operated by a third-party. A remote device 128 may include without limitation, a display in communication with computing device 104, where a display may include any display as described herein. Remote device 128 may include an additional computing device, such as a mobile device, laptop, desktop, computer and the like. A third-party may include any human being, that may care for and/or be involved with an animal. A third-party may include an animal owner, or an employee of an owner who may care for an animal as a part of a job. Computing device 104 may receive a zoological input 124 from a remote device 128 utilizing any network methodology as described herein.

With continued reference to FIG. 1, computing device 104 is configured to select a zoological machine-learning model utilizing a zoological input 124. A "machine-learning model," as used in this disclosure, is a process that automatedly uses a body of data known as "training data" and/or a "training set" to generate an algorithm that will be performed by a computing device 104 to produce outputs given data provided as inputs; this is in contrast to a non-machine-learning software program where the commands to be executed are determined in advance by a user and written in a programming language. A land machine-learning model may be used by computing device 104 to output a property rating factor 136 as described below in more detail.

With continued reference to FIG. 1, a machine-learning model may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include elements of inputs, outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs. Supervised machine-learning processes may include classification algorithms as defined above. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

With continued reference to FIG. 1, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 1, at least a machine-learning process may include a lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data. Heuristic may include selecting some number of highest-ranking associations and/or training data elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

With continued reference to FIG. 1, at least a machine learning process may include a process classifying and/or scoring options according to any criterion used for and/or referred to in any educational inquiry. For instance, and without limitation, at least a machine-learning process may include a mental health suitability classification process and/or scoring algorithm that scores and/or classifies options according to quality and/or availability of mental health supports and/or protocols, as needed by or necessary given biological extraction 108, and/or according to degree of mental health issues in a student body as relevant to biological extraction 108. As a further example, at least a machine-learning process may include a special needs suitability classification process and/or scoring algorithm that scores and/or classifies options according to quality and/or availability of special needs supports and/or protocols, as needed by or necessary given biological extraction 108. As a further example, at least a machine-learning process may include a disability accommodation suitability classification process and/or scoring algorithm that scores and/or classifies options according to quality and/or availability of disability accommodations such as without limitation learning disability accommodations, as needed by or necessary given biological extraction 108.

Continuing to refer to FIG. 1, machine-learning algorithm may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure, Still referring to FIG. 1, machine-learning algorithm may include, without limitation, linear discriminant analysis. Machine-learning algorithm may include quadratic discriminate analysis. Machine-learning algorithm may include kernel ridge regression. Machine-learning algorithm may include support vector machines, including without limitation support vector classification-based regression processes. Machine-learning algorithm may include stochastic gradient descent algorithms, including classification and regression algorithms based on stochastic gradient descent. Machine-learning algorithm may include nearest neighbors algorithms. Machine-learning algorithm may include Gaussian processes such as Gaussian Process Regression. Machine-learning algorithm may include cross-decomposition algorithms, including partial least squares and/or canonical correlation analysis. Machine-learning algorithm may include naïve Bayes methods. Machine-learning algorithm may include algorithms based on decision trees, such as decision tree classification or regression algorithms. Machine-learning algorithm may include ensemble methods such as bagging meta-estimator, forest of randomized tress, AdaBoost, gradient tree boosting, and/or voting classifier methods. Machine-learning algorithm may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

With continued reference to FIG. 1, a "zoological machine-learning model," as used in this disclosure, is a machine-learning model that utilizes a zoological profile 120 as an input and outputs a zoological instruction set 140. Computing device 104 may select a zoological machine-learning model 132 utilizing a zoological input 124. For instance and without limitation, computing device 104 may match a zoological input 124 to a zoological machine-learning model 132 that is related to a zoological input 124. For example, a zoological input 124 that indicates an animal is fed commercial food products may be matched to a zoological machine-learning model 132 intended for commercial food products. Computing device 104 may utilize a zoological profile 120 to select a zoological machine-learning model 132. For example, a zoological profile 120 that identifies a characteristic such as a specific animal breed of a dalmatian dog, may be utilized to select a zoological machine-learning model created for a dalmatian dog.

With continued reference to FIG. 1, computing device 104 may select a zoological machine-learning model 132 by generating an input classifier 136. An "input classifier," as used in this disclosure, is a classifier that utilizes a zoological input 124 as an input and outputs a zoological machine-learning model 132. An input classifier 136 may be generated as any classifier suitable for use as zoological classifier 116 as described above in more detail. An input classifier may be generated utilizing any classification algorithm as described above. Computing device 104 may input zoological input 124 into input classifier 136 and output a zoological machine-learning model 132. Input classifier may utilize training data, including any of the training data as described herein. Training data utilized by input classifier may be generated in any suitable way, including user inputs.

With continued reference to FIG. 1, computing device 104 is configured to calculate a zoological instruction set 140 utilizing zoological machine-learning model 132. A "zoological instruction set," as used in this discourse, is data describing any applicable solution to nourishment requirements, nourishment deficiencies, supplement requirements, and/or supplement deficiencies. A zoological instruction set 140 may recommend one or more nourishment requirements for an animal and may contain one or more suggested meals and/or foods that may fulfill nourishment requirements. A zoological instruction set 140 may recommend one or more supplement requirements for an animal, such as a probiotic tablet a horse may take to diversify the bacteria within the horse's gastrointestinal system.

With continued reference to FIG. 1, computing device 104 is configured to identify in a zoological instruction an alimentary instruction set 144 associated with an animal. An "alimentary instruction set," as used in this disclosure, includes data describing any additional lifestyle recommendations in addition to nutritional and/or supplemental recommendations. An alimentary instruction set 144 may contain one or more activity recommendations, such as a minimum distance an animal such as a dog should be walked each day. An alimentary instruction set 144 may contain one or more condition related recommendations, such as a recommendation that indicates a horse should get a minimum of four hours per day to roam freely outside of a barn. An alimentary instruction set 144 may contain one or more recommendations relating to human interaction, such as a cat that should cuddle with its owner for a minimum of ten minutes each day. One or more lifestyle recommendations may be based on one or more expert inputs relating to animal care and welfare, intended to prolong the life of an animal. One or more expert inputs that may be utilized by computing device 104 to generate zoological instruction set 140 and/or alimentary instruction set 144 may be stored in expert database 148. Expert database 148 may be implemented as any data structure suitable for use as animal database 112 as described above in more detail. Computing device 104 generates an alimentary instruction set 144 contained within zoological instruction set 140.

With continued reference to FIG. 1, computing device 104 is configured to receive an instruction set input 152 from a remote device 128. An "instruction set input," as used in this disclosure, is data describing one or more animal responses and/or one or more third-party responses generated in reference to a zoological instruction set 140. An animal response, may describe how an animal reacted after following nourishment requirements contained within a zoological instruction set 140. An animal response may describe how well an animal tolerated a suggested supplement contained within zoological instruction set 140. A third-party response, may include one or more responses generated by a third-party as to ways in which the third-party fulfilled nourishment and/or supplement requirements contained within a zoological instruction set 140. For example, a third party response may contain a copy of a receipt containing foods that a third-party purchased to feed an animal. In yet another non-limiting example, a third party response may contain the name of commercial animal food that a third-party purchased for an animal, and what quantities of the commercial animal food the third-party fed to the animal. Computing device 104 may evaluate the instruction set input 152 utilizing a zoological instruction set 140. Computing device 104 may evaluate the instruction set input 152, by comparing the instruction set input 152 to a zoological instruction set 140, to determine if the animal and/or the third-party were complaint with the instructions and/or recommendations contained within zoological instruction set 140. For example, computing device 104 may compare a zoological instruction set 140 that recommended increasing the amount of Vitamin C rich foods fed to a dog to increase the dog's immune system, to an instruction set input 152 that indicates a third-party fed a dog foods that included sweet potato, chicken, and mackerel. In such an instance, computing device 104 may identify sweet potato and mackerel as being sources of Vitamin C, based on information contained within expert database 148. Computing device 104 may calculate an updated zoological instruction set 140. Computing device 104 may calculate an updated zoological instruction set 140 utilizing input from expert database 148. Computing device 104 may calculate an updated zoological instruction set 140 that may include further nutritional recommendations if an instruction set input 152 indicates that an animal and/or third party was not compliant with a zoological instruction set 140. Computing device 104 may continue to recommend similar actions if an instruction set input 152 indicates that an animal and/or third party is continuing to be compliant and computing device 104 may recommend one or more further recommendations. For example, an initial zoological instruction set 140 may recommend an animal to get a minimum of 10 minutes of fresh air each day, which may be gradually increased over time to 30 minutes of fresh air each day based on subsequent instruction set input 152 which report that the animal is getting the initially recommended minimum of 10 minutes of fresh air each day.

With continued reference to FIG. 1, computing device 104 is configured to generate a physical performance instruction set 156 utilizing a zoological instruction set 140. A "physical performance instruction set," as used in this disclosure, is data describing one or more ways in which a zoological instruction set 140 may be fulfilled by a physical performance entity. "Fulfillment," as used in this disclosure, is any step and/or process taken in furtherance of a zoological instruction set 140. A step may include ordering a supplement for a lizard from an online pharmacy. Fulfillment may include shopping for commercial cat food at a supermarket. Fulfillment may include ordering one or more ingredients in a recipe for delivery from a food store. Fulfillment may include ordering a meal to be delivered for an animal to a third-party's house. Fulfillment may be completed by a third-party such as a pet owner and/or by a physical performance entity. A "physical performance entity," as used in this disclosure, is any person and/or company that performs fulfillment of a zoological instruction set 140 and/or physical performance instruction set. A physical performance entity may include a home meal delivery service, a grocery delivery service, supplement delivery, vitamin and/or supplement coaching, and/or any other applicable platform configured for the delivery of items relating to food, nutrition, and/or supplements. For instance and without limitation, a physical performance entity may include a vitamin delivery service that delivers vitamins through the mail to a third-party intended for use by the third-party's cat. Computing device 104 transmits a physical performance instruction set 156 to a remote device 128 operated by a physical performance entity. Remote device 128 includes any device as described herein. Computing device 104 transmits a physical performance instruction set 156 to a remote device operated by a physical performance entity utilizing any network methodology as described herein. Computing device 104 may be configured to generate a physical performance instruction to include a frequency datum 160. A "frequency datum," as used in this disclosure, is data describing how often a physical performance instruction set 156 is recommended to be performed. For example, a frequency datum 160 may specify that an animal such as a sheep should receive a one month supply of additional minerals, and that the minerals should be delivered to the sheep for a minimum of the next three months. In yet another non-limiting example, a frequency datum 160 may specify that a cat struggling with anemia should receive iron rich meals delivered from a food service delivery company containing liver twice per day for the next thirty days.

Figure 2:
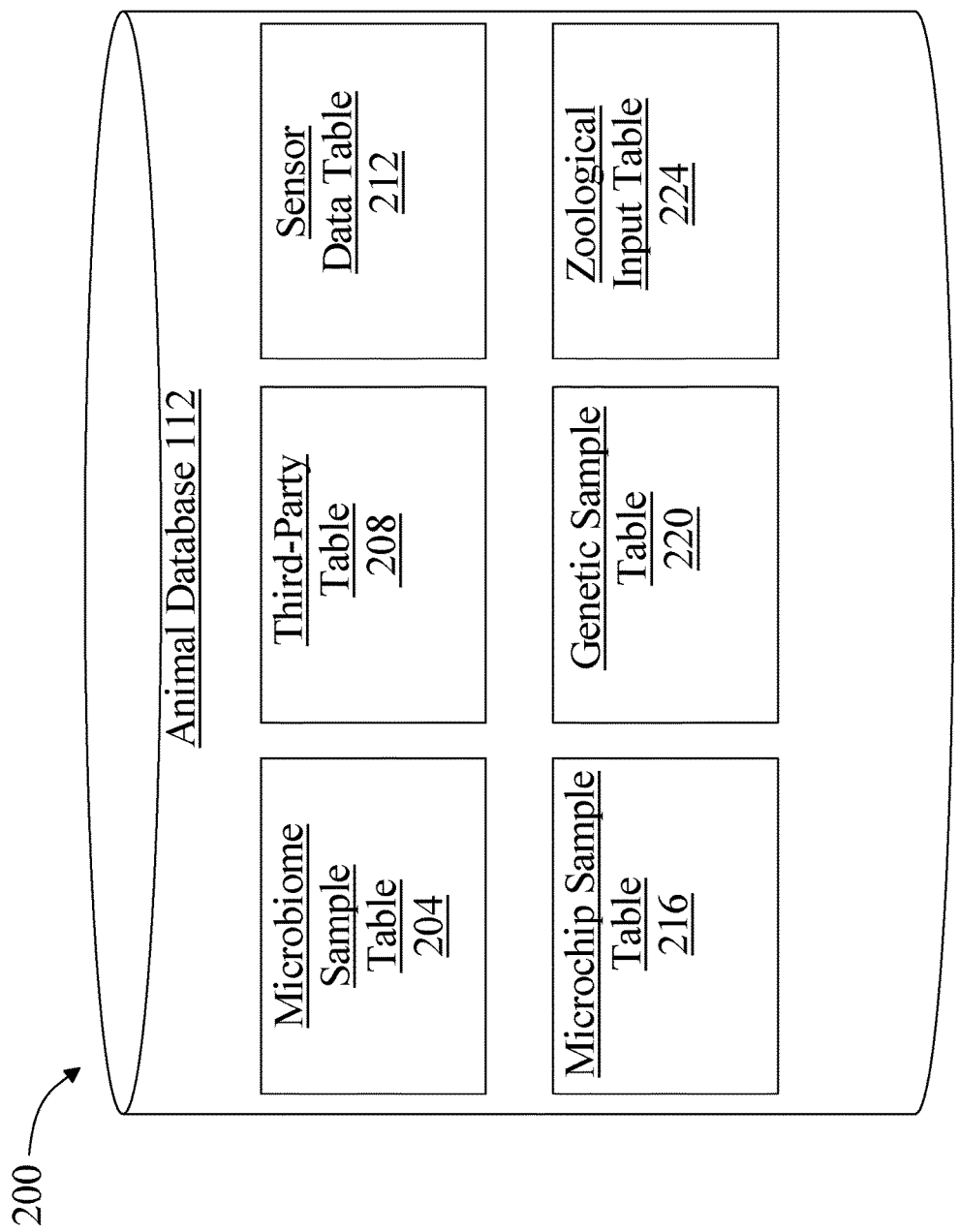
FIG. 2 is a block diagram illustrating an exemplary embodiment of an animal database.

Referring now to FIG. 2, an exemplary embodiment of animal database 112 is illustrated. Animal database 112 may be implemented as any data structure as described above in more detail. One or more tables contained within animal database 112 may include microbiome sample table 204; microbiome sample table 204 may include one or more biological extraction 108 relating to the microbiome. For instance and without limitation, microbiome sample table 204 may include a physically extracted sample such as a stool sample analyzed for the presence of pathogenic species such as parasites and anaerobes. One or more tables contained within animal database 112 may include third-party table 208; third-party table 208 may include one or more data entries identifying third-parties involved in the care of an animal. For instance and without limitation, third-party table 208 may identify an owner of a horse, who provides care to the horse including feeding the horse and taking the horse out for exercise and fresh air. One or more tables contained within animal database 112 may include sensor data table 212; sensor data table 212 may include one or more biological extractions containing sensor measurements. For instance and without limitation, sensor data table 212 may include heart rate, blood pressure, and glucose readings. One or more tables contained within animal database 112 may include microchip sample table 216; microchip sample table 216 may include one or more biological extraction 108 obtained from a microchip. For instance and without limitation, microchip sample table 216 may include an intracellular nutrient level obtained from a microchip embedded under an animal's skin. One or more tables contained within animal database 112 may include genetic sample table 220; genetic sample table 220 may include one or more biological extractions containing genetic samples. For instance and without limitation, genetic sample table 220 may include a blood test analyzed for IGF-1, a gene that codes for insulin-like growth factor 1, which affects stature size of dogs. One or more tables contained within animal database 112 may include zoological input table 224; zoological input table 224 may include one or more zoological input 124 pertaining to an animal. For instance and without limitation, zoological input table 224 may include an input received from an owner, indicating the owner's habit to feed his golden retriever meals made from scratch in the owner's kitchen.

Figure 3:
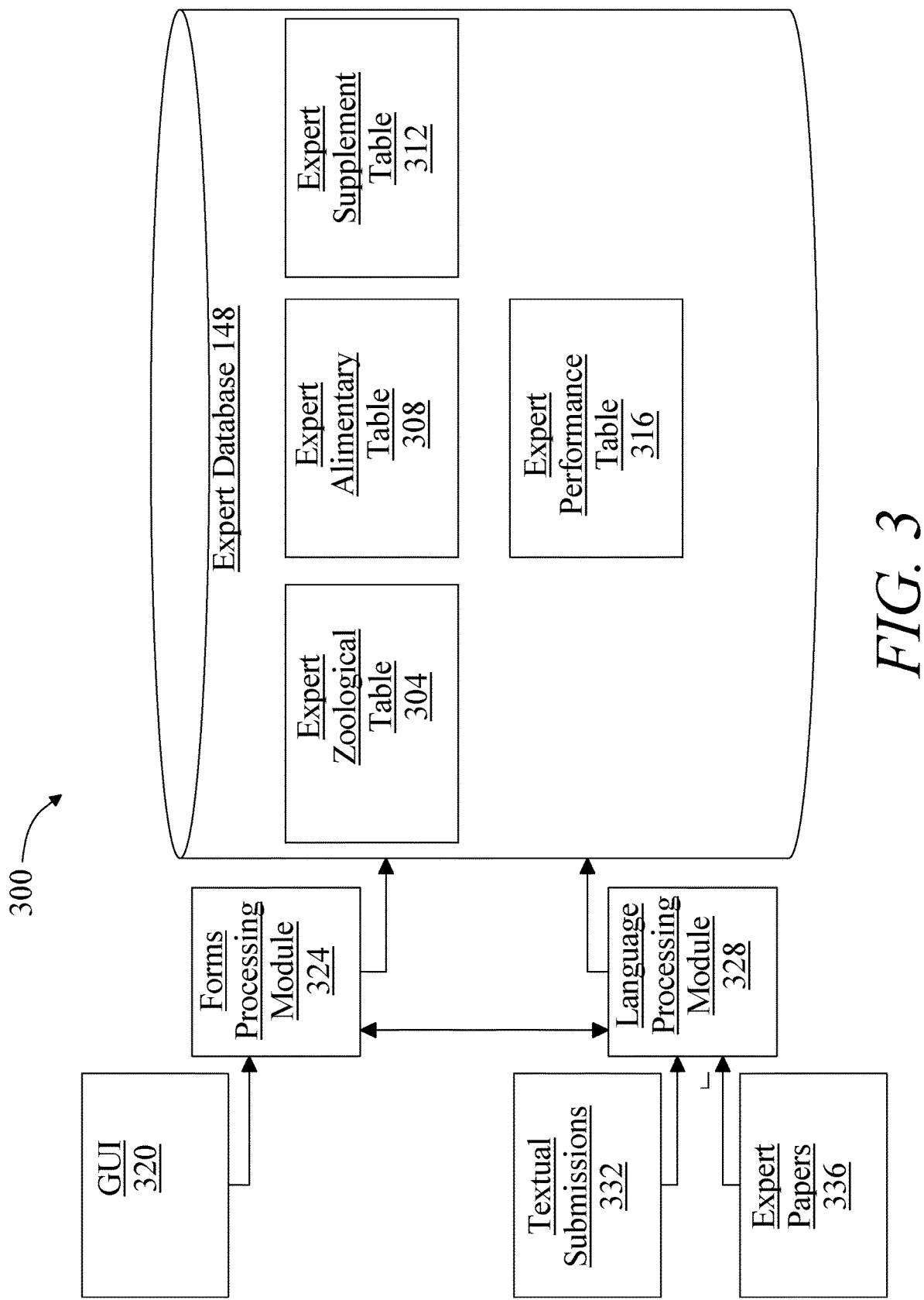
FIG. 3 is a block diagram illustrating an exemplary embodiment of an expert database.

Referring now to FIG. 3, an exemplary embodiment of an expert database 148 is illustrated. Expert database 148 may, as a non-limiting example, organize data stored in the expert database 148 according to one or more database tables. One or more database tables may be linked to one another by, for instance, common column values. For instance, a common column between two tables of expert database 148 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 3, one or more database tables in expert database 148 may include, as a non-limiting example, an expert zoological table 304. Expert zoological table 304 may include any information provided by one or more experts regarding zoological instruction set 140, including any information regarding any nutritional and/or supplemental needs of any animal. One or more database tables in expert database 148 may include, as a non-limiting example, an expert alimentary table 308. Expert alimentary table 308 may include any information provided by one or more experts regarding alimentary instruction sets 144, including for example any information describing any alimentary needs of any animal, such as preferred activity levels of a cat. One or more database tables in expert database 148 may include, as a non-limiting example, an expert supplement table 312. Expert supplement table 312 may include any expert information describing supplement needs of animals, such as supplemental requirements of a lizard. One or more database tables in expert database 148 may include, as a non-limiting example expert performance table 316. Expert performance table 316 may include any information describing physical performances and/or fulfillment as described above in more detail.

In an embodiment, and still referring to FIG. 3, a forms processing module 324 may sort data entered in a submission via a graphical user interface 320 receiving expert submissions by, for instance, sorting data from entries in the graphical user interface 320 to related categories of data; for instance, data entered in an entry relating in the graphical user interface 320 to nutritional requirements of sheep, which may be provided to expert zoological table 304, while data entered in an entry relating to recommended activity levels of ferrets, may be sorted into variables such as expert supplement table 312. Where data is chosen by an expert from pre-selected entries such as drop-down lists, data may be stored directly; where data is entered in textual form, a language processing module may be used to map data to an appropriate existing label, for instance using a vector similarity test or other synonym-sensitive language processing test to map data to existing labels and/or categories. Similarly, data from an expert textual submission 332, such as accomplished by filling out a paper or PDF form and/or submitting narrative information, may likewise be processed using language processing module.

Still referring to FIG. 3, a language processing module 328 may include any hardware and/or software module. Language processing module 328 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 3 language processing module 328 may compare extracted words to categories of data to be analyzed; such data for comparison may be entered on computing device 104 as described above using expert data inputs or the like. In an embodiment, one or more categories may be enumerated, to find total count of mentions in such documents. Alternatively or additionally, language processing module 328 may operate to produce a language processing model. Language processing model may include a program automatically generated by at least a server and/or language processing module 328 to produce associations between one or more words extracted from at least a document and detect associations, including without limitation mathematical associations, between such words, and/or associations between such words and other elements of data analyzed, processed and/or stored by system 100. Associations between language elements, may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of data; positive or negative indication may include an indication that a given document is or is not indicating a category of data.

Still referring to FIG. 3, language processing module 328 and/or computing device 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HIM inference algorithm, such as the forward-backward algorithm or the Viterbi algorithm, may be used to estimate the most likely discrete state given a word or sequence of words. Language processing module 328 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 3, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 3, language processing module 328 may use a corpus of documents to generate associations between language elements in a language processing module 328, and computing device 104 may then use such associations to analyze words extracted from one or more documents. Documents may be entered into computing device 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, computing device 104 may automatically obtain the document using such an identifier, for instance by submitting a request to a database or compendium of documents such as JSTOR as provided by Ithaka Harbors, Inc. of New York.

With continued reference to FIG. 3, data may be extracted from expert papers 336, which may include without limitation publications in medical and/or scientific journals, by language processing module 328 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

Figure 4:
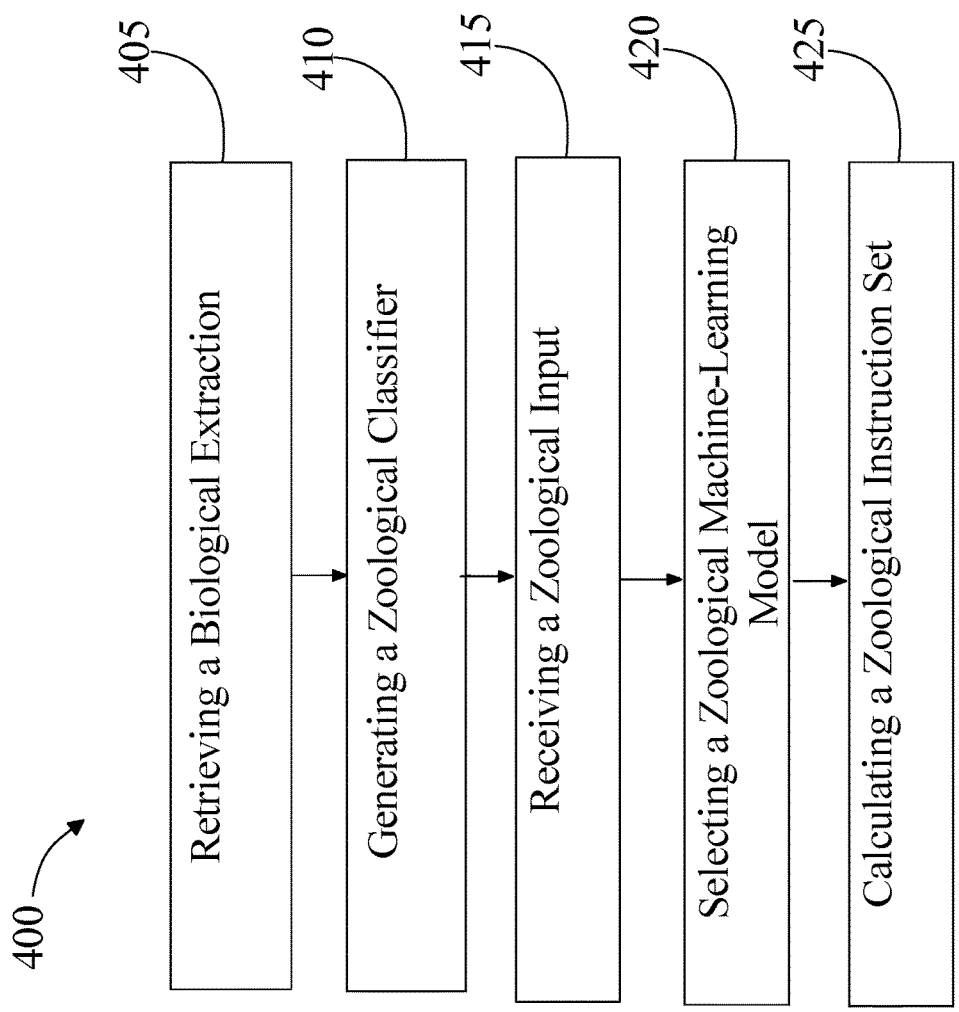
FIG. 4 is a process flow diagram illustrating an exemplary embodiment of an artificial intelligence method of generating zoological instruction sets from biological extractions.

Referring now to FIG. 4, an exemplary embodiment of an artificial intelligence method 400 of generating zoological instruction sets 140 from biological extractions 108 is illustrated. At step 405, a computing device 104 retrieves a biological extraction 108 pertaining to an animal. A biological extraction 108, includes any of the biological extraction 108 as described above in more detail in reference to FIG. 1. A biological extraction 108 may include a blood sample taken from an animal such as a dog, and analyzed for one or more measurements including a hemoglobin level, a packed cell volume hematocrit, a white blood cell count, a platelet count, and a reticulocyte count. In yet another non-limiting example, a biological extraction 108 may include results from an ultrasound performed on a cat. Computing device 104 may retrieve one or more biological extraction 108 pertaining to an animal from animal database 112.

With continued reference to FIG. 4, at step 410, a computing device 104 generates a zoological classifier 116. A zoological classifier 116, includes any of the zoological classifier 116 as described above in more detail in reference to FIG. 1. A zoological classifier 116 may be generated utilizing one or more classification algorithms, including any of the classification algorithms as described above in more detail in reference to FIG. 1. A zoological classifier 116 utilizes a biological extraction 108 as an input and outputs a zoological profile 120. A zoological profile 120 includes data describing one or more animal characteristics and/or traits, attributed to an animal's biological extraction 108. A zoological profile 120 may contain one or more animal characteristics such as if an animal responds well to exercise or if an animal responds best to a specific diet. An animal characteristic and/or trait, may identify one or more attributes that can be expected of a given animal. For instance and without limitation, a zoological profile 120 may identify a cat with a biological extraction 108 showing an elevated hemoglobin A1C level outside of normal limits, as being likely to develop diabetes within a few years. In yet another non-limiting example, a zoological profile 120 may identify a horse with low serotonin levels as being likely to require supplementation with Vitamin D. In yet another non-limiting example, a zoological profile 120 may identify an obese cow as needing extra activity and movement as compared to a nonobese cow. One or more data entries contained within zoological profile 120 may be generated utilizing a classification algorithm and/or one or more entries contained within expert database 148. For example, a leading Veterinarian may submit data into expert database 148 that indicates based on research studies, cats that have elevated fasting blood sugar levels and/or elevated triglycerides respond best to a diet that includes small amounts of canned food given at certain intervals throughout the day instead of one large meal once per day.

With continued reference to FIG. 4, at step 415 a computing device 104 receives a zoological input 124 from a remote device 128. Computing device 104 receives a zoological input 124 from a remote device 128 utilizing any network methodology as described herein. A zoological input 124 includes any of the zoological input 124 as described above in more detail in reference to FIG. 1. A zoological input 124 may be generated by a third-party, such as an owner and/or caregiver of an animal. A zoological input 124 may describe one nutritional and/or supplemental habits of an animal. A zoological input 124 may identify a nourishment element, which may describe one or more habits relating nutrition of an animal. For instance and without limitation, a nourishment element may identify a feeding schedule of an animal, such as how many meals each day the animal receives, and at what time of the day the animal has each meal. In yet another non-limiting example, a nourishment element may identify the constitution of an animal's meals, such as if a third-party prepares meals from scratch in a kitchen, purchases commercial animal food, and/or orders meals or food from a store, meal service, restaurant, grocery store, online store and the like. A zoological input 124 may identify a supplementation element, which may describe one or more supplement habits of an animal. For example, a zoological input 124 may describe any supplements an animal may consume and at what dose and quantity. For example, a zoological input 124 may identify a supplement that an owner gives to a dog each month to prevent the growth of heart worms. In yet another non-limiting example, a zoological input 124 may identify a probiotic supplement an owner gives to cat to prevent the recurrence of a urinary tract infection. One or more zoological input 124 may be stored in animal database 112 as described above in more detail in reference to FIG. 1.

With continued reference to FIG. 4, at step 420, a computing device 104 selects a zoological machine-learning model 132 utilizing a zoological input 124. A zoological machine-learning model 132 includes any of the machine-learning models as described above in more detail in reference to FIG. 1. A zoological machine-learning model 132 utilizes a zoological profile 120 as an input and outputs a zoological instruction set 140. In an embodiment, a zoological machine-learning model 132 may include a supervised machine-learning model, including any of the supervised machine-learning models as described above in more detail in reference to FIG. 1. In an embodiment, a zoological machine-learning model 132 may include an unsupervised machine-learning model, including any of the unsupervised machine-learning models as described above in more detail in reference to FIG. 1. Computing device 104 may select a zoological machine-learning model 132 utilizing a zoological input 124. For instance and without limitation, computing device 104 may select a zoological machine-learning model 132 that outputs zoological instruction set 140 that include recommendations for homecooked meals when a zoological input 124 identifies a zoological habit that includes preparing homecooked meals for an animal. In yet another non-limiting example, computing device 104 may utilize a zoological profile 120 to select a zoological machine-learning model 132. For example, a zoological profile 120 that indicates an animal is likely to develop heart disease due to high levels of low density lipoprotein (LDL) cholesterol may be utilized to select a zoological machine-learning model 132 that contains a zoological profile 120 that matches and/or is similar to the animal's zoological profile 120, and shows a likelihood of developing heart disease.

With continued reference to FIG. 4, computing device 104 may select a zoological machine-learning model 132 utilizing an input classifier 136. Input classifier 136 includes any of the input classifier 136 as described above in more detail in reference to FIG. 1. Input classifier 136 may be implemented as any classifier suitable for use as zoological classified as described above in more detail in reference to FIG. 1. Input classifier 136 utilizes a zoological input 124 as an input and outputs a zoological machine-learning model 132. Input classifier 136 may be generated using one or more classification algorithms, including any of the classification algorithms as described above in more detail in reference to FIG. 1.

With continued reference to FIG. 4, at step 425, a computing device 104 calculates a zoological instruction set 140 utilizing a zoological machine-learning model 132. Zoological instruction set 140 includes any of the zoological instruction sets as described above in more detail in reference to FIG. 1. A zoological instruction set 140 includes data describing any applicable solution to nourishment requirements, nourishment deficiencies, supplement requirements, and/or supplement deficiencies. For instance and without limitation, a zoological instruction set 140 may contain a recommendation of a personalized nutrition plan for the next thirty days for an animal. A zoological instruction set 140 may include a combination of one or more recommended meals, recipes, and/or meal options that can be customized to the needs of an animal. A zoological instruction set 140 may include a recommendation of one or more supplements that may be utilized in combination with one or more nutritional recommendations contained within a zoological instruction set 140. For example, a computing device 104 may recommend nutritional sources of Vitamin C for a cat, thereby reducing the dose of a Vitamin C supplement that may need to be given to the cat, and/or eliminating the need for a Vitamin C supplement at all.

With continued reference to FIG. 4, computing device 104 may generate a zoological instruction set 140 that contains an alimentary instruction set 144. An alimentary instruction set 144 includes any of the alimentary instruction set 144 as described above in more detail in reference to FIGS. 1-3. Computing device 104 may identify within a zoological instruction set 140, an alimentary instruction set 144 associated with an animal. For instance and without limitation, an alimentary instruction set 144 may identify a recommended acupuncture treatment for an animal, such as a cat that may have obsessive compulsive disorder (OCD). In yet another non-limiting example, an alimentary instruction set 144 may identify a recommended exercise routine for a horse, such as needing at least forty five minutes each day of physical activity. In yet another non-limiting example, an alimentary instruction set 144 may identify a recommended medication that may be utilized in combination with a dietary approach to treat hyperthyroidism in a cat. Computing device 104 generates an alimentary instruction set 144 contained within a zoological instruction set 140. Computing device 104 may transmit an alimentary instruction set 144 and/or a zoological instruction set 140 to a remote device 128 utilizing any network methodology as described herein.

With continued reference to FIG. 4, computing device 104 updates zoological instruction set 140 based on feedback from a remote device 128 operated by a third party. Computing device 104 receives an instruction set input 152 from a remote device 128. An instruction set input 152 includes any of the instruction set input 152 as described above in more detail in reference to FIG. 1. In an embodiment, an instruction set input 152 may identify an animal response and/or a third-party response to a zoological instruction set 140. For example, an instruction set input 152 may describe how an animal responded to starting on a gluten free diet, initiated to help reduce symptoms of rheumatoid arthritis. In yet another non-limiting an instruction set input 152 may describe one or more food items that a third-party purchased at a grocery store to prepare one or more recommended meals contained within a zoological instruction set 140. In an embodiment, an instruction set input 152 may describe a food item that an animal may have reacted poorly to after consuming, such as a horse that experienced diarrhea after consuming large quantities of apples. Computing device 104 evaluates an instruction set input utilizing a zoological instruction set 140. Computing device 104 may compare an instruction set input 152 to a zoological instruction set 140 to determine if an animal was compliant and followed one or more recommendations contained within a zoological instruction set 140. Computing device 104 may determine that an instruction set input 152 specifies that an animal was not compliant with one or more supplement recommendations contained within a zoological instruction set 140, and as such computing device 104 may calculate an updated zoological instruction set 140 that recommends initiating the supplement at the same initial dose recommended in a first zoological instruction set 140.

With continued reference to FIG. 4, computing device 104 generates a physical performance instruction set 156 utilizing a zoological instruction set 140 to coordinate fulfillment of a zoological instruction set 140 with physical performance entities. A physical performance instruction set 156 includes any of the physical performance instruction set 156 as described above in more detail in reference to FIG. 1. A physical performance instruction set 156 includes any of the physical performance instruction set 156 as described above in more detail in reference to FIG. 1. Computing device 104 transmits a physical performance instruction set 156 to a remote device 128 operated by a physical performance entity. In an embodiment, computing device 104 may generate a physical performance instruction set 156 that establishes a monthly delivery of multi-vitamins for an animal to be shipped to the residence of the animal through the mail from an online veterinary pharmacy. In such an instance, computing device 104 may transmit a physical performance instruction set 156 to a remote device 128 operated by the veterinary pharmacy with the instructions for the monthly delivery of multi-vitamins. A physical performance instruction set 156 may contain a frequency datum 160, specifying how frequently fulfillment of the physical performance instruction set 156 should occur. For instance and without limitation, a physical performance instruction set 156 may specify that a dog should receive gluten free ingredients for a minimum of the next nine months, to recover from an acute recurrence of an autoimmune condition such as hypothyroidism.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
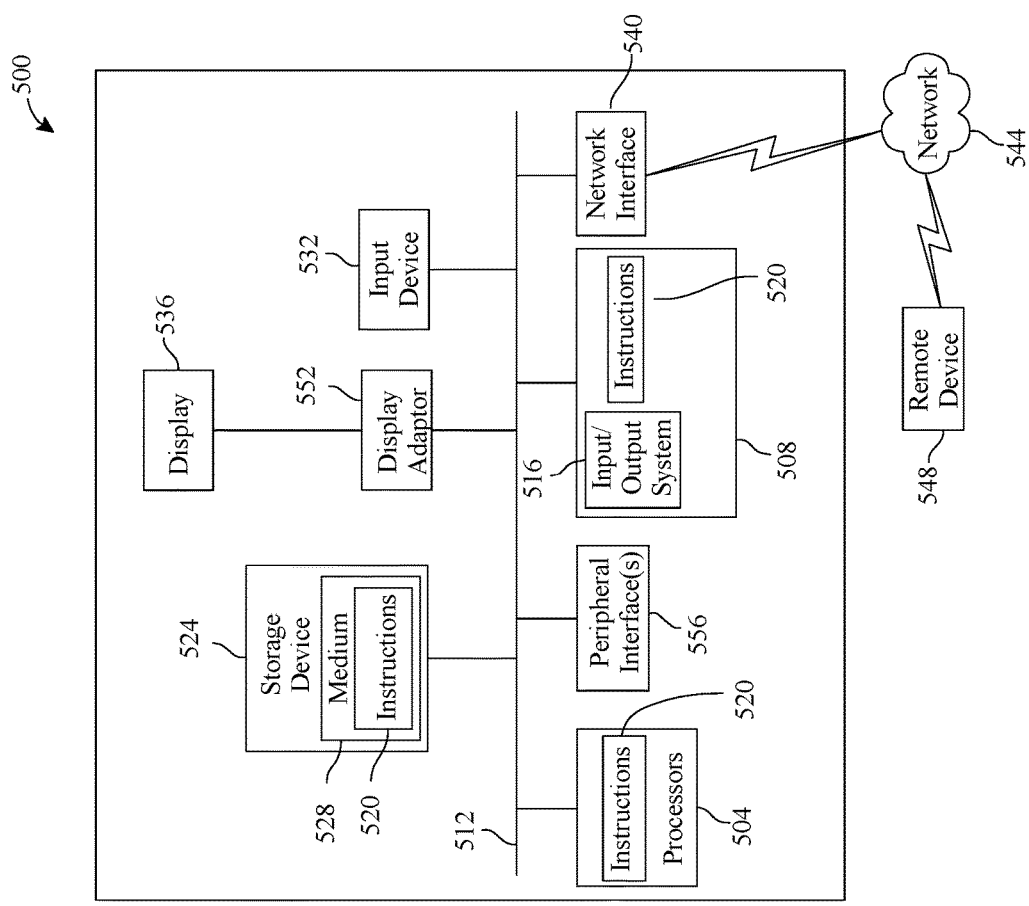
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Memory 508 may include various components (e.g., machine-readable media) including, but not limited to, a random access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIRE-WIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An artificial intelligence system for generating zoological instruction sets from biological extractions, the system comprising a computing device, the computing device designed and configured to:
retrieve a biological extraction pertaining to an animal, wherein the biological extraction comprises a metabolic rate test result that indicates the animal's resting metabolic rate;
generate a zoological classifier wherein the zoological classifier utilizes the biological extraction as an input and outputs a zoological profile, wherein generating the zoological classifier comprises training the zoological classifier with training data, wherein the training data comprises biological extraction data correlated to zoological profile data;
receive a zoological input from a remote device wherein the zoological input identifies a zoological habit;
select a zoological machine-learning model of a plurality of zoological machine-learning models utilizing the zoological input and the zoological profile, wherein:
the zoological machine-learning model comprises a supervised machine learning model;
the zoological machine-learning model utilizes the zoological input and the zoological profile as inputs and outputs a correlated zoological instruction set; and
selecting the zoological machine-learning model comprises:
generating an input classifier;
training the input classifier using input classifier training data comprising a plurality of zoological input data and a plurality of zoological profile data correlated to a plurality of corresponding zoological machine-learning model data;
classifying the zoological input and the zoological profile to the zoological machine-learning model of the plurality of zoological machine-learning model using the trained input classifier; and
selecting the zoological machine-learning model from the plurality of zoological machine-learning models using the trained input classifier and the classification;
train the selected zoological machine-learning model using zoological machine-learning model training data comprising a plurality of zoological input data set and a plurality of zoological profile data set correlated to a plurality of zoological instruction sets;
output the zoological instruction set utilizing the trained selected zoological machine-learning model;
receive an instruction set input from a remote device;
compare the instruction set input and the zoological instruction set; and
update the zoological instruction set as a function of the comparison utilizing the trained selected zoological machine learning model.

2. The system of claim 1, wherein the zoological profile identifies one or more animal characteristics.

3. The system of claim 1, wherein the zoological input identifies a nourishment element.

4. The system of claim 1, wherein the zoological input identifies a supplementation element.

5. The system of claim 1, wherein the computing device selects a zoological machine-learning model by matching an entry contained within a first zoological profile to a second zoological profile contained within the zoological machine-learning model.

6. The system of claim 1, wherein the computing device is further configured to:
identify, in the zoological instruction set, an alimentary instruction set associated with the animal; and
generate an alimentary instruction set contained within the zoological instruction set.

7. The system of claim 1, wherein the computing device is further configured to:
generate a physical performance instruction set utilizing the zoological instruction set; and
transmit the physical performance instruction set to a remote device operated by a physical performance entity.

8. The system of claim 7, wherein the computing device is further configured to generate the physical performance instruction to contain a frequency datum.

9. An artificial intelligence method of generating zoological instruction sets from biological extractions, the method comprising:
retrieving, by a computing device, a biological extraction pertaining to an animal;
generating, by the computing device, a zoological classifier wherein the zoological classifier utilizes the biological extraction as an input and outputs a zoological profile;
receiving, by the computing device, a zoological input from a remote device wherein the zoological input identifies a zoological habit;
selecting, by the computing device, a zoological machine-learning model of a plurality of zoological machine-learning models utilizing the zoological input and the zoological profile, wherein:
the zoological machine-learning model comprises a supervised machine learning model;
the zoological machine-learning model utilizes the zoological input and the zoological profile as inputs and outputs a correlated zoological instruction set; and
selecting the zoological machine-learning model comprises:
generating an input classifier;
training the input classifier using input classifier training data comprising a plurality of zoological input data and a plurality of zoological profile data correlated to a plurality of corresponding zoological machine-learning model data;
classifying the zoological input to the zoological machine-learning model of the plurality of zoological machine-learning model using the trained input classifier; and
selecting the zoological machine-learning model from the plurality of zoological machine-learning models using the trained input classifier and the classification;
training, by the computing device, the selected zoological machine-learning model using zoological machine-learning model training data comprising a plurality of zoological input data set and a plurality of zoological profile data set correlated to a plurality of zoological instruction sets;
outputting, by the computing device, a zoological instruction set utilizing the trained selected zoological machine-learning model;
receiving, by the computing device, an instruction set input from a remote device;

comparing, by the computing device, the instruction set input and the zoological instruction set; and updating, by the computing device, the zoological instruction set as a function of the comparison utilizing the trained selected zoological machine learning model.

10. The method of claim 9, wherein generating the zoological classifier further comprises outputting a zoological profile identifying one or more animal characteristics.

11. The method of claim 9, wherein receiving the zoological input further comprises identifying a nourishment element.

12. The method of claim 9, wherein receiving the zoological input further comprises identifying a supplementation element.

13. The method of claim 9, wherein selecting the zoological machine-learning model further comprises matching an entry contained within a first zoological profile to a second zoological profile contained within the zoological machine-learning model.

14. The method of claim 9, wherein calculating the zoological instruction set further comprises:

identifying, in the zoological instruction set, an alimentary instruction set associated with the animal; and generating an alimentary instruction set contained within the zoological instruction set.

15. The method of claim 9, wherein calculating the zoological instruction set further comprises:

generating a physical performance instruction set utilizing the zoological instruction set; and transmitting the physical performance instruction set to a remote device operated by a physical performance entity.

16. The method of claim 15, wherein generating the physical performance instruction set further comprises generating the physical performance instruction to contain a frequency datum.

\* \* \* \* \*